(12) United States Patent
Seidling et al.

(10) Patent No.: US 8,729,000 B2
(45) Date of Patent: May 20, 2014

(54) SINGLE USE MULTI-PHASE CARE SYSTEM

(75) Inventors: Jeffery Richard Seidling, Neenah, WI (US); Scott W. Wenzel, Neenah, WI (US); Laura Serra, Greenville, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 727 days.

(21) Appl. No.: 11/955,142

(22) Filed: Dec. 12, 2007

(65) Prior Publication Data

US 2009/0156451 A1    Jun. 18, 2009

(51) Int. Cl.
*A61K 8/00*    (2006.01)
*C11D 17/00*    (2006.01)

(52) U.S. Cl.
USPC .......................................... 510/130; 510/417

(58) Field of Classification Search
USPC ................................ 510/130, 417
See application file for complete search history.

(56) References Cited

U.S. PATENT DOCUMENTS

| | | | |
|---|---|---|---|
| 5,827,506 A * | 10/1998 | McShane et al. | 424/59 |
| 5,929,019 A * | 7/1999 | Puvvada et al. | 510/406 |
| 6,534,456 B2 | 3/2003 | Hayward et al. | |
| 6,534,457 B2 * | 3/2003 | Mitra | 510/130 |
| 6,689,223 B1 | 2/2004 | Meine et al. | |
| 6,750,191 B2 * | 6/2004 | Kasturi et al. | 510/417 |
| 7,012,049 B2 | 3/2006 | Littau et al. | |
| 7,135,165 B2 | 11/2006 | Zofchak et al. | |
| 7,820,609 B2 * | 10/2010 | Soffin et al. | 510/130 |
| 2005/0260143 A1 * | 11/2005 | Ryan et al. | 424/53 |
| 2006/0079417 A1 * | 4/2006 | Wagner et al. | 510/130 |

FOREIGN PATENT DOCUMENTS

| | | |
|---|---|---|
| KR | 20-0413144 Y1 | 4/2006 |
| KR | 10-0713993 B1 | 5/2007 |
| KR | 20-0437215 Y1 | 11/2007 |
| WO | 99-07250 A1 | 2/1999 |

OTHER PUBLICATIONS

International Search Report and Written Opinion, PCT/IB2008/054877, 11 pages (Aug. 7, 2009).

* cited by examiner

*Primary Examiner* — Ling Choi
*Assistant Examiner* — Thuy-Ai Nguyen
(74) *Attorney, Agent, or Firm* — Armstrong Teasdale LLP

(57) ABSTRACT

A convenient single use multi-phase care system including multiple formulations can be packaged in one dispensing unit. The multi-phase care system is capable of separately dispensing one of the multiple formulations at a time in a sequential order to allow the consumer to dispense a daily care regimen one step at a time. In one embodiment, the daily care regimen is a multi-phase skin care system. In another embodiment, the daily care regimen is a multi-phase hair care system.

13 Claims, No Drawings

SINGLE USE MULTI-PHASE CARE SYSTEM

BACKGROUND OF DISCLOSURE

The present disclosure generally relates to single use care systems for dispensing at least two separate formulations providing multiple benefits to a user's skin, hair, and/or oral or mucosal areas. Specifically, the present disclosure is directed to a single dispensing unit including a multi-phase skin and/or hair care system, each phase having a separate formulation for providing a benefit to the user's skin, body, and/or hair.

It has become increasingly popular for consumers to use daily product regimens for areas of the body, especially treating the skin and hair. Specifically, for facial treatment and care, consumers typically use multiple formulations for cleansing, toning, and treating the skin of the face. Similarly, hair care regimens can include the multiple steps of shampooing, conditioning, and treating the hair with three or more separate formulations. These separate formulations are generally packaged in multiple bottles and tubes.

Having multiple packages can clutter countertops and make traveling cumbersome, particularly in view of recent airline regulations allowing only a 3-ounce maximum for carry-on liquid products. Additionally, it is difficult, if not impossible, to continuously perform these treatment and care regimens when involved in outdoor activities such as camping. Due to these difficulties and inconveniences, often times, the multi-step care systems are interrupted or completely discontinued. This non-continuous use can many times defeat the purpose of the care system, as generally these products must be used consistently or daily over an extended period of time to obtain the desired results.

As such, there is a need for a compact single use care system including multiple formulations packaged in one dispensing unit that allows the consumer to dispense a daily care regimen one step at a time.

SUMMARY OF THE DISCLOSURE

It has been found that a convenient single use multi-phase care system including multiple formulations can be packaged in one dispensing unit. The multi-phase care system is capable of separately dispensing one of the multiple formulations at a time in a sequential order to allow the consumer to dispense a daily care regimen one step at a time. In one embodiment, the daily care regimen is a multi-phase skin care system including multiple formulations for cleansing, toning, and treating the skin. In another embodiment, the daily care regimen is a multi-phase hair care system including formulations for shampooing, conditioning, and treating the hair.

As such, the present disclosure is directed to a multi-phase care system comprising a dispensing unit. The dispensing unit comprises a first phase comprising a first formulation capable of providing a first benefit and a second phase comprising a second formulation capable of providing a second benefit. The first and second formulations are different formulations that are substantially immiscible. Furthermore, the first and second formulations are not capable of being dispensed from the dispensing unit simultaneously.

The present disclosure is further directed to a multi-phase skin care system comprising a dispensing unit. The dispensing unit comprises a first phase comprising a cleansing formulation and a second phase comprising a toning formulation. The cleansing and toning formulations are different formulations that are substantially immiscible. Furthermore, the cleansing and toning formulations are not capable of being dispensed from the dispensing unit simultaneously.

The present disclosure is further directed to a method of using a multi-phase care system. The method comprises dispensing a first formulation from a dispensing unit; and dispensing a second formulation for the dispensing unit. The first and second formulations are different formulations that are substantially immiscible. Furthermore, the first and second formulations are dispensed sequentially.

Other objects and features will be in part apparent and in part pointed out hereinafter.

DEFINITIONS

Within the context of this specification, each term or phrase below includes the following meaning or meanings:

As used herein, "substantially immiscible" refers to at least two formulations that will not mix to form a single phase, even after long term storage; that is, the substantially immiscible formulations are such that upon dispensing there will still be independent formulations to be dispensed separately. More specifically, the only mixing between the two formulations could potentially be a small amount at the interface of the formulations.

These terms may be defined with additional language in the remaining portions of the specification.

DETAILED DESCRIPTION OF THE DISCLOSURE

The present disclosure is generally related to single use multi-phase care systems for dispensing at least two separate formulations providing multiple benefits to a user's skin, hair, and/or oral or mucosal areas from a single dispensing unit. In one embodiment, the present disclosure is directed to a single dispensing unit including a multi-phase skin care system, each phase having a separate formulation for providing a benefit to the skin. In another embodiment, the present disclosure is directed to a single dispensing unit including a multi-phase hair care system, each phase having a separate formulation for providing a benefit to the hair. It should be understood by a skilled artisan that, while skin and hair care systems will be discussed herein, the multi-phase care systems of the present disclosure can be used for various other daily regimens, such as for example, diaper rash treatment regimens and the like.

Specifically, the multi-phase care systems of the present disclosure include a single dispensing unit. The dispensing unit can be any dispenser known in the art for dispensing liquid formulations and more viscous cream lotions. A variety of dispensing units is known in the art and may be used in conjunction with the multi-phase care systems of the present disclosure. One particularly suitable dispensing unit is a bottle dispenser. Bottle dispensing units for dispensing a liquid formulation are well known. Other suitable dispensing units may include, for example squeeze dispensing units, syringe dispensing units, cartridge dispensing units, and tube-type dispensing units.

As noted above, particularly preferred for use with the multi-phase care systems of the present disclosure are bottle dispensing units. Conventional bottle dispensing units generally comprise a reservoir for storing a liquid and a dispensing head.

Typically, the dispensing units used in the multi-phase care systems of the present disclosure can be any size suitable for use in the particular daily regimen for which the particular multi-phase care system is designed. In light of the recent airline regulations, however, in one embodiment, it is particularly suitable that the dispensing unit be of a size of 3 ounces or smaller. By being this size, the dispensing unit can be easily traveled with in carry-on luggage and smaller bags.

The dispensing unit includes at least a first phase and a second phase. The first phase includes a first formulation providing a benefit to the user. The second phase includes a second formulation providing a benefit to the user. The first phase and second phase are substantially immiscible as described herein above. Specifically, the first phase and second phase remain as separate phase (i.e., do not mix) even when subjected to vibrations, shaking, or other type of mechanical energy due to manipulation of the dispensing unit by the consumer or in transport of the product.

The first and second phases are typically independently selected to be one of a hydrophobic phase, hydrophilic phase, a siliphilic phase, or combinations thereof. To keep the first and second phase of the multi-phase care system from mixing upon use of the care system, the phases to be added to the dispensing unit must be selected to be substantially immiscible as described above. When the first and/or second phases are a combination of hydrophobic, hydrophilic, and/or siliphilic phases, the external phase of the first phase must not be miscible with the external phase of the second phase. Furthermore, it should be recognized by one skilled in the art that, while the phases must be selected to be substantially immiscible with one another, as the phases are dispensed from a single dispensing unit, the phases must be formulated as such to allow for dispensing from the same dispensing unit.

By way of example, in one embodiment, the first phase is a hydrophobic phase and the second phase is a hydrophilic phase. In an alternative embodiment, the first phase is a hydrophilic phase and the second phase is a hydrophobic phase. In yet another embodiment, the first phase is selected from the group consisting of an emulsion consisting of both a hydrophobic phase and a hydrophilic phase, which could vary with which of these phases is the external phase depending on the type of emulsion. In either case, the second phase is a siliphilic phase. As the second phase is a siliphilic phase; that is, a phase which is substantially high in silicone and prefers to interact with other silicones, the second phase will be immiscible with either the hydrophobic or hydrophilic phases. The above list should be interpreted as examples and should not in any way limit the scope of the suitable phases for use as the first phases and second phases respectfully.

In one embodiment, the multi-phase care system contains more than two phases. For example, it may be preferable to produce a multi-phase care system having three phases, four phases, or even, five phases or more. As with the first and second phases above, the third, fourth, fifth phases (and all other phases if more than five phases are selected) should be selected to be substantially immiscible with the phase in which it is directly contacted within the dispensing unit.

As noted above, the first phase comprises a first formulation typically capable of providing a first benefit to a user. For example, in one embodiment, when the multi-phase care system is a skin care system, the first formulation provides a first skin care benefit. Similarly, the second formulation is typically capable of providing a second benefit to a user. In the multi-phase skin care system, the second formulation provides a second skin care benefit. It should be understood by one skilled in the art, that while the first formulation and second formulation can independently provide any benefit known in the art of the particular care system, in each particular multi-phase care system, the first formulation and second formulation are different formulations and thus, provide different benefits to the user. Simply restated, the first benefit, provided by the first formulation, is different from the second benefit, provided by the second formulation.

Furthermore, as with the first phase and second phase, if more than two phases are used in the multi-phase care system, such as a third, fourth, and fifth phase (and more phases if more than five phases are desired), it should be recognized that the additional phases should include formulations, each independently being capable of providing additional benefits to a user. For example, if a first, second, and third phase are included in the multi-phase care system, the first phase includes a first formulation providing a first benefit, the second phase includes a second formulation providing a second benefit, and the third phase includes a third formulation providing a third benefit. Likewise, if the multi-phase care system included additional phases, such as a fourth and fifth phase, the fourth and fifth phases must include fourth and fifth formulations, providing fourth and fifth benefits, respectively.

In an alternative embodiment, the multi-phase care system can include more than two phases and can be configured such to provide a multiple day regimen. Without being limiting, in one example, the multi-phase care system provides hair care for multiple days and, as such, a first phase includes, for example, a cleansing formulation, a second phase includes a conditioning formulation, a third phase includes the same cleansing formulation as the first phase, and a fourth phase includes the same conditioning formulation as the second phase.

As with the first and second formulations described above, the third, fourth, and fifth formulations are each different from any of the other formulations in the multi-phase care system (including the first and second formulations). Moreover, as the third, fourth, and fifth formulations are different formulations, while being capable of providing any benefit known in the art of the particular care system, in each particular multi-phase care system, the first formulation, second formulation, third formulation, fourth formulation, fifth formulation, and so forth are different formulations and thus, provide different benefits to the user.

While providing different benefits, it should be understood to one of skill in the art that the formulations may include overlapping components; that is, the formulations may include some of the same components.

Typically, the formulations for use in the phases of the multi-phase care system can include, for example, hydrophilic delivery vehicles such as gels, serums, hydroalcoholics, hydrophobic delivery vehicles such as anhydrous oils, and combinations such as hydrophobic/hydrophilic combinations (e.g., oil-in-water emulsions (O/W), water-in-oil emulsions (W/O), water-in-oil-in-water emulsions (W/O/W), oil-in-water-in-oil emulsions (O/W/O)) and hydrophilic/siliphilic or hydrophobic/siliphilic combinations (e.g., water-in-silicone emulsions (W/S), water-in-silicone-in-water emulsions (W/S/W), glycol in silicone emulsions (G/S)), and the like, and combinations thereof.

In one particularly preferred embodiment, the multi-phase care system is a skin care system, in which the first formulation provides a first skin care benefit and the second formulation provides a second skin care benefit. In embodiments in which more than two phases and thus formulations are used, it should be understood that each additional formulation will provide a separate and distinct skin care benefit.

A skin care benefit includes any beneficial effect on the skin and/or any improvement of skin feel and/or aesthetics. Without being limiting, examples of formulations providing skin care benefits can include formulations for cleansing, toning, treatment, finishing, and the like.

When the formulation is a cleansing formulation, the cleansing formulation may be in any form known in the art, such as, for example, hand soaps, body soaps, body washes, shampoos, surface cleaners, dish soaps, facial cleansers, hand washes, and the like. These types of cleansing formulations typically include at least one foaming agent, such as a surfactant. Although discussed herein primarily in terms of a surfactant, it should be understood that the cleansing formulations of the present disclosure may comprise other cleansing agents, and need not comprise a surfactant. For example, in certain embodiments, the formulations may comprise a thickener, a swellable clay, a foaming agent (which may or may not comprise a surfactant), and optionally a solvent or other carrier. Examples of such formulations include, for example, hand sanitizers, lotions, anti-microbial formulations, and the like.

As noted above, the cleansing formulations of multi-phase care systems of the present disclosure may comprise a foaming agent, such as a surfactant, as well as a thickener, and a swellable clay. Upon dispensing the cleansing formulation from a bottle or other similar dispensing unit and/or upon application of shear, the cleansing formulation will produce foam that may be used for cleansing applications. Although discussed primarily in terms of a surfactant, it is to be understood that the foaming agent may be an agent other than a surfactant. For example, alternately or in addition to surfactants, the foaming agent may comprise emulsifiers, ethoxylated skin conditioning agents, solubilizers, derivatized silicone polymers, and combinations thereof. Typically, the cleansing formulation comprises a foaming agent in an amount of from about 0.1% (by weight) to about 40% (by weight), more preferably about 0.3% (by weight) to about 25% (by weight), and still more preferably about 0.5% (by weight) to about 15% (by weight). The foaming agent is included in the cleansing formulation to provide a cleaning, lathering, and/or foaming action during use of the multi-phase care system.

As used herein, "by weight" refers to the total weight of the formulation. For example, if the cleansing formulation has a total weight of 100 grams and comprises 90% (by weight) foaming agent, the cleansing formulation comprises 90 grams of foaming agent. As will be recognized by those skilled in the art, some commercially available surfactants (and thickeners or other formulation components) are sold as a solution; e.g., a certain percentage of surfactant in water. If such a solution is used to produce a formulation, it is to be understood that the percent (by weight) of the surfactant (or other component) given herein is referring to the percent (by weight) of the actual surfactant (or other component) in the final formulation, not the percent (by weight) of the surfactant plus water solution.

Suitable surfactants for use in the cleansing formulation include anionic surfactants, amphoteric surfactants, cationic surfactants, zwitterionic surfactants, non-ionic surfactants, and combinations thereof.

Suitable anionic surfactants include, for example, alkyl sulfates, alkyl ether sulfates, alkyl aryl sulfonates, alpha-olefin sulfonates, alkali metal or ammonium salts of alkyl sulfates, alkali metal or ammonium salts of alkyl ether sulfates, alkyl phosphates, silicone phosphates, alkyl glyceryl sulfonates, alkyl sulfosuccinates, alkyl taurates, acyl taurates, alkyl sarcosinates, acyl sarcosinates, sulfoacetates, alkyl phosphate esters, mono alkyl succinates, monoalkyl maleates, sulphoacetates, acyl isethionates, alkyl carboxylates, phosphate esters, sulphosuccinates (e.g., sodium dioctylsulphosuccinate), and combinations thereof. Specific examples of anionic surfactants include sodium lauryl sulphate, sodium lauryl ether sulphate, ammonium lauryl sulphosuccinate, ammonium lauryl sulphate, ammonium lauryl ether sulphate, sodium dodecylbenzene sulphonate, triethanolamine dodecylbenzene sulphonate, sodium cocoyl isethionate, sodium lauroyl isethionate, sodium N-lauryl sarcosinate, and combinations thereof.

Suitable cationic surfactants include, for example, alkyl ammonium salts, polymeric ammonium salts, alkyl pyridinium salts, aryl ammonium salts, alkyl aryl ammonium salts, silicone quaternary ammonium compounds, and combinations thereof. Specific examples of cationic surfactants include behenyltrimonium chloride, stearlkonium chloride, distearalkonium chloride, chlorohexidine diglutamate, polyhexamethylene biguanide (PHMB), cetyl pyridinium chloride, benzammonium chloride, benzalkonium chloride, and combinations thereof.

Suitable amphoteric surfactants include, for example, betaines, alkylamido betaines, sulfobetaines, N-alkyl betaines, sultaines, amphoacetates, amophodiacetates, imidazoline carboxylates, sarcosinates, acylamphoglycinates, such as cocamphocarboxyglycinates and acylamphopropionates, and combinations thereof. Specific examples of amphoteric surfactants include cocamidopropyl betaine, lauramidopropyl betaine, meadowfoamamidopropyl betaine, sodium cocoyl sarcosinate, sodium cocamphoacetate, disodium cocoamphodiacetate, ammonium cocoyl sarcosinate, sodium cocoamphopropionate, and combinations thereof.

Suitable zwitterionic surfactants include, for example, alkyl amine oxides, silicone amine oxides, and combinations thereof. Specific examples of suitable zwitterionic surfactants include, for example, 4-[N,N-di(2-hydroxyethyl)-N-octadecylammonio]-butane-1-carboxylate, S—[S-3-hydroxypropyl-5-hexadecylsulfonio]-3-hydroxypentane-1-sulfate, 3-[P,P-diethyl-P-3,6,9-trioxatetradexopcylphosphonio]-2-hydroxypropane-1-phosphate, 3-[N,N-dipropyl-N-3-dodecoxy-2-hydroxypropylammonio]-propane-1-phosphonate, 3-(N,N-dimethyl-N-hexadecylammonio)propane-1-sulfonate, 3-(N,N-dimethyl-N-hexadecylammonio)-2-hydroxypropane-1-sulfonate, 4-[N,N-di(2-hydroxyethyl)-N-(2-hydroxydodecyl)ammonio]-butane-1-carboxylate, 3-[S-ethyl-S-(3-dodecoxy-2-hydroxypropyl)sulfonio]-propane-1-phosphate, 3-[P,P-dimethyl-P-dodecylphosphonio]-propane-1-phosphonate, 5-[N,N-di(3-hydroxypropyl)-N-hexadecylammonio]-2-hydroxy-pentane-1-sulfate, and combinations thereof.

Suitable non-ionic surfactants include, for example, mono- and di-alkanolamides such as, for example, cocamide MEA and cocamide DEA, amine oxides, alkyl polyglucosides, ethoxylated silicones, ethoxylated alcohols, ethoxylated carboxylic acids, ethoxylated amines, ethoxylated amides, ethoxylated alkylolamides, ethoxylated alkylphenols, ethoxylated glyceryl esters, ethoxylated sorbitan esters, ethoxylated phosphate esters, glycol stearate, glyceryl stearate, and combinations thereof. It will be recognized by one skilled in the art that many of the nonionic surfactants described herein may act to improve the foaming properties of the cleansing formulation of the multi-phase care system, and may provide a more compact, reduced bubble size or creamy foam.

The cleansing formulations may also comprise a thickener, which acts to thicken or increase the viscosity of the cleansing formulation. Typically, the formulation will comprise from about 0.01% (by weight) to about 5% (by weight) of thickener.

A variety of thickeners may be used in the cleansing formulations described herein. In one embodiment, the thickener may be a cellulosic thickener or gum. Examples of suitable cellulosic or gum thickeners include xanthan gum, agar, alginates, carrageenan, furcellaran, guar, cationic guar, gum arabic, gum tragacanth, karaya gum, locust bean gum, dextran, starch, modified starches, gellan gum, carboxymethylcellulose, hydroxypropylcellulose, hydroyethylcellulose, propylene glycol alginate, hydroxypropyl guar, amylopectin, cellulose gum, chitosan, modified chitosan, hydroxypropyl methylcellulose, microcrystalline cellulose, silica, fumed silica, colloidal silica, dehydroxanthan gum, non-acrylic based carbomers, and combinations thereof. When the thickener is a cellulosic or gum thickener, the thickener is preferably present in the cleansing formulation in an amount of from about 0.01% (by weight) to about 2% (by weight), and more preferably in an amount of from about 0.1% (by weight) to about 1% (by weight).

Alternately or in addition, the thickener may be an acrylic based polymer. Non-limiting examples of suitable acrylic based polymer thickeners include acrylates/$C_{10}$-$C_{30}$ alkyl acrylate crosspolymers, certain carbomers, acrylates copolymers, aminoacrylates copolymers, and combinations thereof. Examples of commercially available acrylic based polymer thickeners include Structure® Plus (National Starch & Chemical, Bridgewater, N.J.), which is an acrylates/aminoacrylates/$C_{10-30}$ alkyl PEG-20 itaconate copolymer, Carbopol® Aqua SF-1 Polymer (Noveon, Cleveland Ohio), which is an acrylates copolymer, Pemulen® TR-1 and TR-2 and Carbopol® ETD 2020 (available from Noveon), which are acrylates/C10-30 alkyl acrylates crosspolymers, and the Carbopol® Ultrez series of polymers (available from Noveon), which are carbomers. When the thickener is an acrylic based polymer, the thickener is preferably present in the cleansing formulation in an amount of from about 0.1% (by weight) to about 5% (by weight).

The cleansing formulations may optionally be formulated using an acid-sensitive thickener and/or a base-sensitive thickener. As the names suggest, acid-sensitive thickeners are activated (i.e., swell or "thicken") upon contact with an acidic agent, while base-sensitive thickeners are activated upon contact with an alkaline agent. One advantage of using acid and/or base sensitive thickeners in the cleansing formulations is improved ease of processing. For instance, acid or base sensitive thickeners may be more readily dispersed in a formulation when in a non-activated state than when in an activated (or "thickened") state. Thus, an acid- or base-sensitive thickener may be combined with other formulation components prior to activation, and activated by contact with an acidic or alkaline agent after the acid- or base-sensitive thickener is dispersed throughout the formulation.

Examples of suitable acid-sensitive thickeners for use in the cleansing formulations include the Structure® Plus (National Starch & Chemical, Bridgewater, N.J.) thickener, described above. The acid-sensitive thickeners may be activated by contact with any of a wide range of acidic agents including, for example, glycolic acid, lactic acid, phosphoric acid, citric acid, other organic acids, and similar acidic agents. Acid sensitive thickeners are generally activated over a pH range of from about 3 to about 9, and more typically over a pH range of from about 3 to about 7. The Structure® Plus thickener is typically activated over a pH range of from about 3 to about 9.

Examples of suitable base-sensitive thickeners include the Carbopol® Aqua SF-1 Polymer (Noveon, Cleveland Ohio) thickener, described above, as well as the Pemulen® TR-1 and TR-2 thickeners (available from Noveon), the Carbopol® ETD 2020 thickeners (available from Noveon), and the Carbopol® Ultrez series of thickeners (available from Noveon), all described above, and other carbomers and starches, and combinations thereof. The base-sensitive thickeners may be activated by contact with any of a wide range of alkaline agents including, for example, various metal hydroxides and amines, and other similar alkaline agents. Non-limiting examples of suitable metal hydroxides include potassium hydroxide and sodium hydroxide. Non-limiting examples of suitable amines include triethanolamine, diethanolamine, monoethanolamine, tromethamine, aminomethylpropanol, triisopropanolamine, diisopropanolamine, tetrahydroxypropylethylenediamine, and PEG-15 cocoamine. Base sensitive thickeners are generally activated over a pH range of from about 5 to about 11, and more typically over a pH range of from about 6 to about 11.

In certain embodiments, the cleansing formulations may include two or more different types of thickeners. For instance, the cleansing formulations may include any combination of cellulosic thickeners, gum thickeners, acid-sensitive thickeners, base-sensitive thickeners, and/or acrylic based polymer thickeners.

The cleansing formulations may additionally comprise a swellable clay. The swellable clay may act as a thixotropic agent, giving the cleansing formulation its shear-thinning properties, while allowing the formulation to remain sufficiently viscous to suspend particles therein when under low or no shear.

A variety of clays are suitable for use in the cleansing formulations described herein including, for example, bentonite, laponite, hectorite, montmorillonite, beidellite, saponite, stevensite, magnesium aluminum silicate, other aluminum silicates, as well as various other natural and/or synthetic clays, and combinations thereof. Typically, the cleansing formulations will comprise from about 0.01% (by weight) to about 10% (by weight) and more preferably from about 0.1% (by weight) to about 5% (by weight) of a swellable clay. In one embodiment, the cleansing formulation may comprise from about 0.01% (by weight) to less than about 5% (by weight) of a swellable clay.

Additional suitable agents for use in the cleansing formulation may include humectants, preservatives, fragrances, chelating agents, and combinations thereof.

A skin care system of the present disclosure may further include a second phase including a second formulation, wherein the second formulation is a toning formulation. Toning formulations provide such benefits as closing pores of a user's skin, restoring the natural pH of the skin (typically, a pH of from about 5.0 to about 5.5), removing skin impurities (e.g., dirt, oils, sebum, make-up, pollutants, and the like), hydrating the skin, and generally preparing the skin for treatment using a treatment formulation as described below.

Generally, toning formulations for skin care include astringents, humectants, carriers, and combinations thereof. Suitable astringents include, for example, ethanol, witch hazel, rose water, alum, oatmeal, yarrow, bayberry, cold water, rubbing alcohol, astringent preparations such as silver nitrate, zinc oxide, zinc sulfate, Burow's solution, tincture of benzoin, and vegetable substances such as tannic and gallic acid, and combinations thereof. As used herein, the term "cold water" refers to water having a temperature below room temperature (approximately 25° C. (77° F.)).

Suitable humectants include, for example, glycerin, glycerin derivatives, sodium hyaluronate, betaine, amino acids, glycosaminoglycans, honey, sorbitol, glycols, polyols, sugars, hydrogenated starch hydrolysates, salts of PCA, lactic acid, lactates, and urea. A particularly preferred humectant is glycerin.

Carriers for the toning formulations can be any carrier material typically known in the cosmetic and medical arts as a basis for ointments, lotions, creams, salves, aerosols, gels, suspensions, sprays, foams, and the like, and may be used in their art-established levels. In one particular embodiment, the carrier is an aqueous carrier. With an aqueous carrier, the toning formulation may include water in an amount of from about 30% (by weight) to about 95% (by weight). In another embodiment, the carrier is an alcohol carrier. The alcohol carrier can be any suitable alcohol. One particularly preferred alcohol is ethanol. With an alcohol carrier, the toning formulation may include alcohol in an amount of from about 30% (by weight) to about 95% (by weight).

Other suitable carriers can also be used in the toning formulations. In certain embodiments, the carriers themselves can provide the skin care benefit. Non-limiting examples of suitable carriers include emollients, sterols or sterol derivatives, natural and synthetic fats or oils, polyols, surfactants, esters, silicones, and other pharmaceutically acceptable carrier materials.

In a further embodiment, the multi-phase skin care system includes a third phase including a third formulation. The third formulation may include a treatment formulation for treating the skin. It should be understood that, while it is described herein that the first phase comprises a cleansing formulation, the second phase comprises toning formulation, and the third phase comprises a treatment formulation, the various formulations can be used in any of the phases of the multi-phase care system without departing from the scope of the disclosure. For example, the first phase may comprise a cleansing formulation and the second phase may comprise a treatment formulation. The specific compositions of the various phases will depend upon the end daily regimen desired.

Typically, the treatment formulation includes a treatment agent that is known to have a treating effect on the skin such as reducing fine lines and wrinkles, improving the evenness of skin tone, and reduction of acne. More specifically, the treatment agent can be selected from the group consisting of appearance modifying agents (e.g., tooth whitening agents, exfoliating agents, skin-firming agents, anti-callous agents, anti-acne agents, anti-aging agents, anti-wrinkle agents, anti-dandruff agents, antiperspirant agents, wound care agents, enzyme agents, scar repair agents, humectant agents, hair care agents such as conditioners, styling agents, and detangling agents), therapeutic agents, pharmaceuticals (e.g., drugs, anti-oxidants, transdermal drug delivery agents, botanical extracts, vitamins, magnets, magnetic metals, and foods), xenobiotics, skin coloration agents (e.g., tanning agents, lightening agents, and brightening agents, shine control agents and drugs), shine control agents, colorant agents, surface conditioning agents (e.g., pH adjusting agents, moisturizers, skin conditioners, exfoliation agents, shaving lubricants, skin-firming agents, anti-callous agents, anti-acne agents, anti-aging agents, anti-wrinkle agents, anti-dandruff agents, wound care agents, skin lipids, enzymes, scar care agents, humectants, powders, botanical extracts, and drugs) external analgesic agents, anti-inflammatory (e.g., anti-irritant agents, anti-allergy agents, wound care agents, transdermal drug delivery, and drugs), fragrances, odor neutralizing agents, soothing agents, calming agents, antiperspirants, deodorants, botanical extracts (e.g., peppermint oil, eucalyptol, eucalyptus oil, camphor, and tea tree oil), peptides, natural and synthetic fats or oils, moisture absorbers, and combinations thereof. Additionally, the conditioning agents and skin toning agents, as described more fully herein, can be used as treatment agents in the formulations.

The term "natural fat or oil" is intended to include fats, oils, essential oils, essential fatty acids, non-essential fatty acids, phospholipids, and combinations thereof. Suitable fats and oils include Apricot Kernel Oil, Avocado Oil, Babassu Oil, Borage Seed Oil, Butter, C12-C18 Acid Triglyceride, Camellia Oil, Canola Oil, Caprylic/Capric/Lauric Triglyceride, Caprylic/Capric/Linoleic Triglyceride, Caprylic/Capric/Stearic Triglyceride, Caprylic/Capric Triglyceride, Carrot Oil, Cashew Nut Oil, Castor Oil, Cherry Pit Oil, Chia Oil, Cocoa Butter, Coconut Oil, Cod Liver Oil, Corn Germ Oil, Corn Oil, Cottonseed Oil, C10-C18 Triglycerides, Egg Oil, Epoxidized Soybean Oil, Evening Primrose Oil, Glyceryl Triacetyl Hydroxystearate, Glyceryl Triacetyl Ricinoleate, Glycosphingolipids, Grape Seed Oil, Hazelnut Oil, Human Placental Lipids, Hybrid Safflower Oil, Hybrid Sunflower Seed Oil, Hydrogenated Castor Oil, Hydrogenated Castor Oil Laurate, Hydrogenated Coconut Oil, Hydrogenated Cottonseed Oil, Hydrogenated C12-C18 Triglycerides, Hydrogenated Fish Oil, Hydrogenated Lard, Hydrogenated Menhaden Oil, Hydrogenated Mink Oil, Hydrogenated Orange Roughy Oil, Hydrogenated Palm Kernel Oil, Hydrogenated Palm Oil, Hydrogenated Peanut Oil, Hydrogenated Shark Liver Oil, Hydrogenated Soybean Oil, Hydrogenated Tallow, Hydrogenated Vegetable Oil, Lanolin and Lanolin Derivatives, Lard, Lauric/Palmitic/Oleic Triglyceride, Lesquerella Oil, Linseed Oil, Macadamia Nut Oil, Maleated Soybean Oil, Meadowfoam Seed Oil, Menhaden Oil, Mink Oil, Moringa Oil, Mortierella Oil, Neatsfoot Oil, Oleic/Linoleic Triglyceride, Oleic/Palmitic/Lauric/Myristic/Linoleic Triglyceride, Oleostearine, Olive Husk Oil, Olive Oil, Omental Lipids, Orange Roughy Oil, Palm Kernel Oil, Palm Oil, Peach Kernel Oil, Peanut Oil, Pengawar Djambi Oil, Pentadesma Butter, Phospholipids, Pistachio Nut Oil, Placental Lipids, Rapeseed Oil, Rice Bran Oil, Safflower Oil, Sesame Oil, Shark Liver Oil, Shea Butter, Soybean Oil, Sphingolipids, Sunflower Seed Oil, Sweet Almond Oil, Tall Oil, Tallow, Tribehenin, Tricaprin, Tricaprylin, Triheptanoin, Trihydroxymethoxystearin, Trihydroxystearin, Triisononanoin, Triisostearin, Trilaurin, Trilinolein, Trilinolenin, Trimyristin, Trioctanoin, Triolein, Tripalmitin, Trisebacin, Tristearin, Triundecanoin, Vegetable Oil, Walnut Oil, Wheat Bran Lipids, Wheat Germ Oil, Zadoary Oil, oil extracts of various other botanicals, and other vegetable or partially hydrogenated vegetable oils, and the like, as well as mixtures thereof.

Suitable fatty acids include Arachidic Acid, Arachidonic Acid, Behenic Acid, Capric Acid, Caproic Acid, Caprylic Acid, Coconut Acid, Corn Acid, Cottonseed Acid, Hydrogenated Coconut Acid, Hydrogenated Menhaden Acid, Hydrogenated Tallow Acid, Hydroxystearic Acid, Isostearic Acid, Lauric Acid, Linoleic Acid, Linolenic Acid, Linseed Acid, Myristic Acid, Oleic Acid, Palmitic Acid, Palm Kernel Acid, Pelargonic Acid, Ricinoleic Acid, Soy Acid, Stearic Acid, Tall Oil Acid, Tallow Acid, Undecanoic Acid, Undecylenic Acid, Wheat Germ Acid, and the like, as well as mixtures thereof.

Suitable essential oils include Anise Oil, Balm Mint Oil, Basil Oil, Bee Balm Oil, Bergamot Oil, Birch Oil, Bitter Almond Oil, Bitter Orange Oil, Calendula Oil, California Nutmeg Oil, Caraway Oil, Cardamom Oil, Chamomile Oil, Cinnamon Oil, Clary Oil, Cloveleaf Oil, Clove Oil, Coriander Oil, Cypress Oil, Eucalyptus Oil, Fennel Oil, Gardenia Oil, Geranium Oil, Ginger Oil, Grapefruit Oil, Hops Oil, Hyptis Oil, Indigo Bush Oil, Jasmine Oil, Juniper Oil, Kiwi Oil, Laurel Oil, Lavender Oil, Lemongrass Oil, Lemon Oil, Linden Oil, Lovage Oil, Mandarin Orange Oil, Matricaria Oil, Musk Rose Oil, Nutmeg Oil, Olibanum, Orange Flower Oil, Orange Oil, Patchouli Oil, Pennyroyal Oil, Peppermint Oil, Pine Oil, Pine Tar Oil, Rose Hips Oil, Rosemary Oil, Rose Oil, Rue Oil, Sage Oil, Sambucus Oil, Sandalwood Oil, Sassafras Oil, Silver Fir Oil, Spearmint Oil, Sweet Marjoram Oil, Sweet Violet Oil, Tar Oil, Tea Tree Oil, Thyme Oil, Wild Mint Oil, Yarrow Oil, Ylang Ylang Oil, and the like, as well as mixtures thereof.

Some preferred natural fats and oils include, but are not limited to Avocado Oil, Apricot Oil, Babassu Oil, Borage Oil, Camellia oil, Canola oil, Castor Oil, Coconut oil, Corn Oil, Cottonseed Oil, Evening Primrose Oil, Hydrogenated Cottonseed Oil, Hydrogenated Palm Kernel Oil, Maleated Soybean Oil, Meadowfoam Oil, Palm Kernel Oil, Phospholipids, Rapeseed Oil, Palmitic Acid, Stearic Acid, Linoleic Acid, Rose Hip Oil, Sunflower Oil, Soybean Oil, PROLIPID 141 (proprietary blend of Glyceryl Stearate, Fatty Acids, Lecithin, and Phospholipids from International Specialty Products, Wayne, N.J.) and the like, as well as mixtures thereof.

The term "synthetic fat or oil" is intended to include synthetic fats and oils, esters, silicones, other emollients, and combinations thereof. Examples of suitable synthetic fats or oils include petrolatum and petrolatum based oils, mineral oils, mineral jelly, isoparaffins, polydimethylsiloxanes such as methicone, cyclomethicone, dimethicone, dimethiconol, trimethicone, alkyl dimethicones, alkyl methicones, alkyldimethicone copolyols, organo-siloxanes (i.e., where the organic functionality can be selected from alkyl, phenyl, amine, polyethylene glycol, amine-glycol, alkylaryl, carboxal, and the like), silicones such as silicone elastomer, phenyl silicones, alkyl trimethylsilanes, dimethicone crosspolymers, cyclomethicone, gums, resins, fatty acid esters (esters of C6-C28 fatty acids and C6-C28 fatty alcohols), glyceryl esters and derivatives, fatty acid ester ethoxylates, alkyl ethoxylates, C12-C28 fatty alcohols, C12-C28 fatty acids, C12-C28 fatty alcohol ethers, propylene glycol esters and derivatives, alkoxylated carboxylic acids, alkoxylated alcohols, fatty alcohols, Guerbet alcohols, Guerbet Acids, Guerbet Esters, and other cosmetically acceptable emollients.

Specific examples of suitable esters may include, but are not limited to, cetyl palmitate, stearyl palmitate, cetyl stearate, isopropyl laurate, isopropyl myristate, isopropyl palmitate, and combinations thereof.

The lipid phase described above may optionally include a ceramide or ceramide derivative, such as glucosylceramides, acylceramide, bovine ceramides, sphingolipid E, and combinations thereof.

In one embodiment, in addition to the first phase, second phase, and third phase, the multi-phase care system includes a fourth phase, the fourth phase including a finishing formulation. As with the first three phases, it should be understood that the various formulations described herein can be used in any of the phases of the multi-phase care system without departing from the scope of the disclosure.

When included, the finishing formulation comprises a finishing agent that typically delivers moisturization or a moisture-barrier for sealing in moisture to the user. Specifically, the finishing agent can be any moisturizing agent and/or moisture-barrier enhancing agent known in the art.

Additionally, the finishing agent may be capable of providing aesthetic benefits such as skin smoothing or a powdery feel. Examples of additional suitable finishing agents include skin conditioning agents (e.g., pH adjusting agents, moisturizers, skin conditioners, exfoliation agents, shaving lubricants, skin-firming agents, anti-callous agents, anti-acne agents, anti-aging agents, anti-wrinkle agents, anti-dandruff agents, wound care agents, skin lipids, enzymes, scar care agents, humectants, powders, botanical extracts, and drugs), fragrances, botanical extracts, powders, and combinations thereof.

In another embodiment, as noted above, the multi-phase care system is a hair care system. In one specific embodiment, the multi-phase hair care system includes a dispensing unit, as described above, including a first phase and a second phase. The first phase may include a cleansing formulation as described above for the skin care system, and the second phase may comprise a conditioning formulation.

The conditioning formulation typically includes any formulation that is capable of replenishing hair with conditioning agents that make the hair easier to comb, impart body and shine, and promote healthy looking hair. Suitable conditioning agents for use in the conditioning formulation include quaternium compounds, emollients, moisturizers, humectants, and combinations thereof.

Similar to the multi-phase skin care system described above, the multi-phase hair care system in one embodiment can further include a third phase. The third phase of one particularly preferred embodiment includes a treatment formulation. The treatment formulation may include treatment agents such as described for the skin care system. Moreover, the treatment formulation may include additional treatment agents that are more specific for hair care. Examples of such treatment agents include detangling agents, hair growth promoters, soothing agents, calming agents, and combinations thereof.

In addition to the first, second, and third phases, the multi-phase hair care system can include a fourth phase such as a phase including a finishing formulation similar to the multi-phase skin care system described above. As with the finishing formulation described in relation to the skin care system, the finishing formulation for the multi-phase hair care system can include any finishing agent for moisturizing or holding moisture within the hair. Exemplary agents are described above for the multi-phase skin care system. Additionally, the finishing formulation may include finishing agents such as styling agents, fragrances, botanical extracts, and combinations thereof.

It should be understood that while described in the instant specification as containing cleansing formulations, toning formulations, conditioning formulations, treatment formulations, and finishing formulations, the multi-phase care systems of the present disclosure can include any formulations capable of providing a benefit to the user's skin, hair, body, and the like. The type of formulation will depend upon the desired multi-phase care system and the specific daily regimen needed by the user.

The multi-phase care systems of the present disclosure can further include agents for distinguishing the phases within the dispensing units. Specifically, different colors and or textures of the formulations can be made to visually separate the multiple phases. In one embodiment, one or more of the above-described phases includes at least one visual enhancer that may be selected from the group consisting of a coloring agent and a liquid crystal. The coloring agents may comprise dyes, color additives, pigments, and/or lakes that may be included in at least one formulation in unencapsulated form or optionally may be encapsulated, as described herein, in a suitable encapsulant. Suitable dyes include, for example, Blue 1, Blue 4, Brown 1, External Violet 2, External Violet 7, Green 3, Green 5, Green 8, Orange 4, Orange 5, Orange 10, Orange 11, Red 4, Red 6, Red 7, Red 17, Red 21, Red 22, Red 27, Red 28, Red 30, Red 31, Red 33, Red 34, Red 36, Red 40, Violet 2, Yellow 5, Yellow 6, Yellow 7, Yellow 8, Yellow 10, Yellow 11, Acid Red 195, Anthocyanins, Beetroot Red, Bromocresol Green, Bromothymol Blue, Capsanthin/Capsorubin, Curcumin, and Lactoflavin.

Suitable color additives include, for example, aluminum powder, annatto, bismuth citrate, bismuth oxychloride, bronze powder, caramel, carmine, beta carotene, chloraphyllin-copper complex, chromium hydroxide green, chromium oxide greens, copper powder, disodium EDTA-copper, ferric ammonium ferrocyanide, ferric ferrocyanide, guauazulene, guanine, henna, iron oxides, lead acetate, manganese violet, mica, pyrophylite, silver, titanium dioxide, ultramarines, zinc oxide, and combinations thereof.

Suitable pigments or lakes include, for example, Blue 1 Lake, External Yellow 7 Lake, Green 3 Lake, Orange 4 Lake, Orange 5 Lake, Orange 10 Lake, Red 4 Lake, Red 6 Lake, Red 7 Lake, Red 21 Lake, Red 22 Lake, Red 27 Lake, Red 28 Lake, Red 30 Lake, Red 31 Lake, Red 33 Lake, Red 36 Lake, Red 40 Lake, Yellow 5 Lake, Yellow 6 Lake, Yellow 7 Lake, Yellow 10 Lake, and combinations thereof.

In another embodiment, the coloring agent may be a colored bead, such as a particulate polymeric material to which a coloring agent is attached, or added. Optionally, the coloring agent may comprise a colored encapsulant, in which one or more additives may optionally be encapsulated. Examples of colored encapsulants include the LipoSpheres™ and Lipo-Beads™ products described below.

As noted above, in certain embodiments, the coloring agents may be encapsulated in an encapsulant, such as a shell material or polymer matrix, prior to being formulated into the composition. Micro or nano capsules may be used to gradually release the agents upon an increase in temperature or physical contact, such as when the formulation is contacted with the skin of a user. Suitable encapsulation shell or matrix materials include cellulose-based polymeric materials (e.g., ethyl cellulose), carbohydrate-based materials (e.g., cationic starches and sugars), polyglycolic acid, polylactic acid, and lactic acid-based aliphatic polyesters, and materials derived therefrom (e.g., dextrins and cyclodextrins) as well as other materials compatible with human tissues.

The micro or nano encapsulation shell thickness may vary depending upon the composition of the formulation, and is generally manufactured to allow the encapsulated agent to be covered by a thin layer of encapsulation material, which may be a monolayer or thicker laminate layer, or may be a composite layer. The encapsulation layer should be thick enough to resist cracking or breaking of the shell during handling or shipping of the product. The encapsulation layer should be constructed such that humidity from atmospheric conditions during storage, shipment, or wear will not cause a breakdown of the microencapsulation layer and result in a release of the coloring agent.

Micro and nano encapsulants suitable for use in producing the coloring agents of the present disclosure may also be commercially obtained. For example, LipoBeads™ products (available from Lipo Technologies, Inc.) are colored beads of a uniform spherical semi-solid matrix of lactose or mannitol microcrystalline cellulose and hydroxypropyl methyl cellulose that may contain hydrophilic or hydrophobic core materials, such as vitamins, natural oils, and antibacterial agents, among others. LipoBeads™ may have an average size of either 700 microns or 1500 microns. LipoSphere™ products (available from Lipo Technologies, Inc.) comprise multiple droplets of hydrophobic and/or hydrophilic material entrapped in a polymer matrix of alginate, agar, or gelatin. The LipoSphere™ products may have a size of from 400 to 4000 microns. LipoCapsule™ gelatin products (available from Lipo Technologies, Inc.) consist of a clear, non-pigmented shell surrounding a hydrophobic core material. The shell may be comprised of gelatin, polyoxymethylene urea, or methoxymethyl methylol melamine. The LipoCapsule™ products may have a size of from 5 to 3000 microns. Other commercially available encapsulated agents include NanoSal™ nanospheres, which are solid hydrophobic nanospheres having an average particle size of 0.01 to 1 micron, which may be used to encapsulate a variety of additives.

When used, the coloring agents can be included within one or more of the formulations in an amount of from about 0.001% (by weight) to about 10% (by weight), and more suitably, from about 0.01% (by weight) to about 5% (by weight).

In an alternative embodiment, one or more liquid crystals can be used as the visual enhancer to differentiate the multiple phases within the multi-phase care system. One particularly suitable example of a liquid crystal is ISP Colorflow™ 100 (available from International Specialty Products). Specifically, ISP Colorflow™ 100 is produced by combining cholesteryl oleyl carbonate, cholesteryl chloride, cholesteryl nonanoate, and butylated hydroxytoluene.

When used, the liquid crystals can be included within one or more of the formulations in an amount of from about 0.01% (by weight) to about 5% (by weight).

The thickness of each of phase in the multi-phase care system will typically depend upon the desired care system and the desired formulations for use in the daily regimen. As the multi-phase care system is intended to be a single use system, the overall size and amount of product will need to remain small to ensure that each phase and formulation can be utilized fully.

In addition to the multi-phase care system, the present disclosure is also directed to methods for using the multi-phase care system in a daily regimen. Generally, the method includes: dispensing from a dispensing unit a first formulation; and dispensing from the dispensing unit a second formulation. Specifically, as noted above, the first and second formulations are different formulations and are substantially immiscible. As such, the first and second formulations remain separate within the dispenser and are further separately and sequentially dispensed from a single dispensing unit in a daily regimen. Specifically, the first formulation is dispensed from the dispensing unit and then the second formulation is dispensed from the same dispensing unit. Even more specifically, the first and second formulations are sequentially dispensed from the same opening within the dispensing unit.

In one embodiment, the method of using the multi-phase care system further includes dispensing a third formulation from the single dispensing unit. The third formulation is a different formulation and is substantially immiscible with the second formulation; that is the third formulation will not substantially mix with the second formulation, in which it is in direct contact. Furthermore, the third formulations are dispensed from the dispensing unit sequentially from both the first and second formulation; that is, the third formulation is not simultaneously dispensed with either the first and/or second formulations. Specifically, the multi-phase care system is used by first dispensing the first formulation, then the second formulation, and finally, dispensing the third formulation.

Furthermore, in another embodiment, the method of using the multi-phase care system further includes dispensing a fourth formulation from the single dispensing unit. The fourth formulation, similar to the first, second, and third formulations, is a different formulation and is substantially immiscible with the third formulation; that is the fourth formulation will not substantially mix with the third formulation, in which it is in direct contact. Furthermore, the fourth formulations are not dispensed from the dispensing unit simultaneously with any of the first, second, and/or third formulations. Specifically, use of the multi-phase care system is typically performed by first dispensing the first formulation, then the second formulation, then the third formulation, and finally, dispensing the fourth formulation.

As described more fully above, less than or more than four formulations can be used in the multi-phase care system without departing from the scope of the present disclosure.

The present disclosure is illustrated by the following example which is merely for the purpose of illustration and is not to be regarded as limiting the scope of the disclosure or manner in which it may be practiced.

EXAMPLE 1

In this example, a multi-phase skin care system is produced for use in accordance with the present disclosure.

Specifically, three phases are produced to provide a daily regimen for skin cleansing, exfoliating, and finishing. To produce the multi-phase skin care system, a two-ounce clear tube-type dispensing unit is first loaded with the first phase including a first toner formulation. The first toner formulation is in the form of a carbomer gel with suspended colored beads. Specifically, the first phase is introduced into the dispensing unit closest to the opening of the dispensing unit.

A second phase, including a second treating (e.g., exfoliating) formulation, is then introduced into the dispensing unit and is stacked on top of the first phase. The second phase is an anhydrous sugar scrub.

Finally, the third phase, including a third finishing formulation, is then introduced into the dispensing unit and is stacked on top of the second phase. The third formulation is an oil-in-water emulsion.

Upon use, the first phase is initially pumped out of the dispensing unit, followed by the second phase, and finally, followed by the third phase. The first, second, and third formulations used in the first, second, and third phase, respectively, are shown in Tables 1-3 below.

TABLE 1

First Formulation

| Component | % w/w | Grams | Function of Component |
|---|---|---|---|
| Water | 93.77 | 468.85 | Solvent |
| Carbopol Ultrez 21 (The Lubrizol Corp., Cleveland, OH) | 0.3 | 1.5 | Rheology modifier |
| Gycerin | 5.0 | 25 | Humectant |
| Kathon CG (Rohm and Haas, Philadelphia, PA) | 0.03 | 0.15 | Preservative |
| Solubilisant LRI (Sensient Cosmetic Tech., France) | 0.6 | 3.0 | Solubilizer |
| Fragrance | 0.3 | 1.5 | Fragrance |
| Potassium hydroxide | pH to 6.0* | | pH adjustment |
| Colored Beads (Lipobeads, available from Lipo Chemical, Inc. (Paterson, New Jersey)) | 0.3 | 1.5 | Aesthetics |

*Potassium hydroxide was added to the first formulation until the pH of the first formulation reached 6.0.

TABLE 2

Second Formulation

| Component | % w/w | Grams | Function of Component |
|---|---|---|---|
| Versagel MC (Penreco, The Woodlands, TX) | 44.7 | 223.5 | Solvent/Suspending Agent |
| Hydrogenated polydecene | 15 | 75 | Emollient |
| $C_{12-15}$ Alkyl Benzoate | 15 | 75 | Emollient |
| Sugar | 25 | 125 | Exfolliant Agent |
| Fragrance | 0.3 | 1.5 | Fragrance |

TABLE 3

Third Formulation

| Component | % w/w | Grams | Function of Component |
|---|---|---|---|
| A | | | |
| Cetearyl Olivate/Sorbitan Olivate | 2.5 | 12.5 | Emulsifier |
| Oliwax LC (B&T Srl., Italy) | 0.5 | 2.5 | Oil Phase Thickener |
| Shea Butter | 3.0 | 15 | Emollient |
| Dicaprylyl Carbonate | 3.0 | 15 | Emollient |
| Avocado Oil | 10 | 50 | Emollient |
| B | | | |
| Deionized Water | 73.75 | 368.75 | Solvent |
| Glycerine | 3.0 | 15 | Humectant |
| Propylene Glycol | 3.0 | 15 | Humectant |
| Sodium Polyacrylate | 0.65 | 3.25 | Rheology Modifier |
| C | | | |
| Fragrance | 0.3 | 1.5 | Fragrance |
| Kathon CG (Rohm and Haas, Philadelphia, PA) | 0.3 | 1.5 | Preservative |

The first formulation was produced by first adding water to a beaker, then dispersing the Carbopol Ultrez 21 (i.e., carbomer) with agitation until fully hydrated. Once hydrated, the glycerin and Kathon CG were added to the beaker. A premix of fragrance and Solubilisant LRI was then added to the formulation and mixed until homogenous. The colored beads were also added to the formulation during mixing. Finally, the pH of the formulation was adjusted to 6.0 using potassium hydroxide.

To produce the second formulation, all ingredients were mixed in a beaker until homogenous.

The third formulation was produced by first dispersing the polyacrylates (from composition "B") in water (also from composition "B"). Add the remaining components of composition "B" and mix until homogenous. Compositions "A" and "B" were then separately heated to a temperature of about 70° F. (21.1° C.) and then combined. The combined mixture was then mixed until homogeneous. The homogenized mixture was allowed to cool to a temperature below 40° F. (4.4° C.) and then composition "C" was added. As with the first formulation, the pH of the third formulation can be adjusted as necessary to reach at pH of 6.0.

Having described the invention in detail, it will be apparent that modifications and variations are possible without departing from the scope of the disclosure defined in the appended claims.

When introducing elements of the present disclosure or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the disclosure are achieved and other advantageous results attained.

As various changes could be made in the above products without departing from the scope of the disclosure, it is intended that all matter contained in the above description and shown in the accompanying drawings shall be interpreted as illustrative and not in a limiting sense.

What is claimed is:

1. A multi-phase care system, the care system comprising:
    a dispensing unit comprising:
        a first phase comprising a first formulation capable of providing a first benefit; and
        a second phase comprising a second formulation capable of providing a second benefit, wherein the first and second formulations are different formulations that are substantially immiscible and are not capable of being dispensed from the dispensing unit simultaneously, wherein one of the first formulation or the second formulation is a cleaning formulation comprising a thickener in an amount of from about 0.01% (by weight) to about 5% (by weight) of thickener.

2. The multi-phase care system as set forth in claim 1 wherein the first phase and second phase are independently selected from the group consisting of a hydrophobic phase, a hydrophilic phase, an emulsion comprising a hydrophobic phase and a hydrophilic phase, a siliphilic phase, and an emulsion comprising a siliphilic phase.

3. The multi-phase care system as set forth in claim 2 wherein the first phase is a hydrophilic phase and the second phase is a hydrophobic phase.

4. The multi-phase care system as set forth in claim 2 wherein the first phase is a hydrophobic phase and the second phase is a hydrophilic phase.

5. The multi-phase care system as set forth in claim 2 wherein the first phase is selected from the group consisting of a hydrophobic phase, a hydrophilic phase, an emulsion comprising an hydrophobic phase and a hydrophilic phase, and the second phase is a siliphilic phase.

6. The multi-phase care system as set forth in claim 1 wherein one of the first formulation or the second formulation is a cleansing formulation comprising at least one surfactant.

7. The multi-phase care system as set forth in claim 6 wherein one of the first formulation or the second formulation is a treatment formulation comprising a treatment agent selected from the group consisting of appearance modifying agents, exfoliating agents, wound care agents, scar repair agents, therapeutic agents, pharmaceuticals, xenobiotics, detangling agents, skin coloration agents, shine control agents, hair growth promoters, colorant agents, anti-dandruff agents, anti-inflammatory agents, fragrances, odor neutralizing agents, soothing agents, calming agents, antiperspirants, deodorants, botanical extracts, peptides, natural and synthetic fats and oils, moisture absorbers, conditioning agents, skin toning agents, and combinations thereof.

8. The multi-phase care system as set forth in claim 1 wherein the dispensing unit further comprises a third phase being in direct contact with the second phase and comprising a third formulation capable of providing a third benefit, wherein the third formulation is a different formulation and is substantially immiscible with the second formulation, and wherein the third formulation is not capable of being dispensed from the dispensing unit simultaneously with either of the first formulation or second formulation.

9. The multi-phase care system as set forth in claim 8 wherein the first phase, second phase, and third phase are independently selected from the group consisting of a hydrophobic phase, a hydrophilic phase, an emulsion comprising a hydrophobic phase and a hydrophilic phase, a siliphilic phase, and an emulsion comprising a siliphilic phase.

10. The multi-phase care system as set forth in claim 8 wherein at least one of the first formulation, second formulation, or third formulation is a finishing formulation comprising a finishing agent selected from the group consisting of moisturizing agents, moisture-barrier enhancing agents, skin conditioning agents, styling agents, fragrances, botanical extracts, powders, and combinations thereof.

11. The multi-phase care system as set forth in claim 8 wherein the dispensing unit further comprises a fourth phase being in direct contact with the third phase and comprising a fourth formulation capable of providing a fourth benefit, wherein the fourth formulation is a different formulation and is substantially immiscible with the third formulation, and wherein the fourth formulation is not capable of being dispensed from the dispensing unit simultaneously with any of the first, second, or third formulations.

12. The multi-phase care system as set forth in claim 1 wherein the first and second formulations further independently comprise a visual enhancer.

13. A multi-phase skin care system, the skin care system comprising:
    a dispensing unit comprising:
        a first phase comprising a cleansing formulation;
        a second phase comprising a toning formulation, wherein the cleansing formulation and the toning formulation are different formulations that are substantially immiscible and are not capable of being dispensed from the dispensing unit simultaneously, and wherein the cleansing formulation comprises a thickener in an amount of from about 0.01% (by weight) to about 5% (by weight) of thickener; and wherein the toning formulation comprises an astringent selected from the group consisting of ethanol, witch hazel, rose water, alum, oatmeal, yarrow, bayberry, cold water, rubbing alcohol, silver nitrate, zinc sulfate, Burow's solution, tincture of benzoin, tannic acid, gallic acid, and combinations thereof.

* * * * *

UNITED STATES PATENT AND TRADEMARK OFFICE
CERTIFICATE OF CORRECTION

PATENT NO. : 8,729,000 B2
APPLICATION NO. : 11/955142
DATED : May 20, 2014
INVENTOR(S) : Jeffrey Richard Seidling et al.

It is certified that error appears in the above-identified patent and that said Letters Patent is hereby corrected as shown below:

In the Specification

In Column 6, Lines 32-33, delete "[S-3-hydroxypropyl-5-hexadecylsulfonio]" and insert -- [S-3-hydroxypropyl-S-hexadecylsulfonio] -- therefor.

In the Claims

In Claim 1, Column 17, Line 24, delete "cleaning" and insert -- cleansing -- therefor.

Signed and Sealed this
Nineteenth Day of May, 2015

Michelle K. Lee
*Director of the United States Patent and Trademark Office*